United States Patent [19]
Bruno

[11] Patent Number: 5,251,009
[45] Date of Patent: Oct. 5, 1993

[54] INTERFEROMETRIC MEASURING ARRANGEMENT FOR REFRACTIVE INDEX MEASUREMENTS IN CAPILLARY TUBES

[75] Inventor: Alfredo E. Bruno, Oberwil, Switzerland

[73] Assignee: Ciba-Geigy Corporation, Ardsley, N.Y.

[21] Appl. No.: 12,610

[22] Filed: Feb. 2, 1993

Related U.S. Application Data

[63] Continuation of Ser. No. 641,192, Jan. 15, 1991, abandoned.

[30] Foreign Application Priority Data

Jan. 22, 1990 [CH] Switzerland .................. 185/90

[51] Int. Cl.$^5$ .................................. G01B 9/02
[52] U.S. Cl. ............................ 356/361; 356/128; 356/246
[58] Field of Search ............... 356/361, 128, 246, 73.1

[56] References Cited

U.S. PATENT DOCUMENTS

| 3,529,896 | 9/1970 | Padawer . | |
|---|---|---|---|
| 4,227,806 | 10/1980 | Watkins | 356/73.1 |
| 4,441,811 | 4/1984 | Melezoglu et al. | 356/128 |
| 4,605,305 | 8/1986 | Lenoir et al. | 356/246 |

FOREIGN PATENT DOCUMENTS

| 0101733 | 5/1988 | Japan . | |
|---|---|---|---|
| 1318859 | 6/1987 | U.S.S.R. | 356/361 |

OTHER PUBLICATIONS

Applied Optics, vol. 16, No. 4, pp. 1050-1053 Apr./1977.
Applied Optics, vol. 11, No. 4 pp. 953-954 Apr./1972.
Anal. Chem., vol. 58, pp. 504-505 (1986).
Applied Optics, vol. 22, No. 22 pp. 3526-3531 Nov./1983.

Primary Examiner—Samuel A. Turner
Attorney, Agent, or Firm—JoAnn Villamizar; William A. Teoli, Jr.; Marla J. Mathias

[57] ABSTRACT

A detection cell (4) is part of an interferometer for measuring changes in the refractive index of a medium located in a capillary (2). In order to simplify the evaluation of an interference fringe pattern, the capillary (2) is arranged in a matching fluid (15), the refractive index of which corresponds to that of the material of the capillary. The matching fluid (15) acts at the same time as a temperature-control bath for the capillary, thereby substantially increasing the temperature stability.

15 Claims, 6 Drawing Sheets

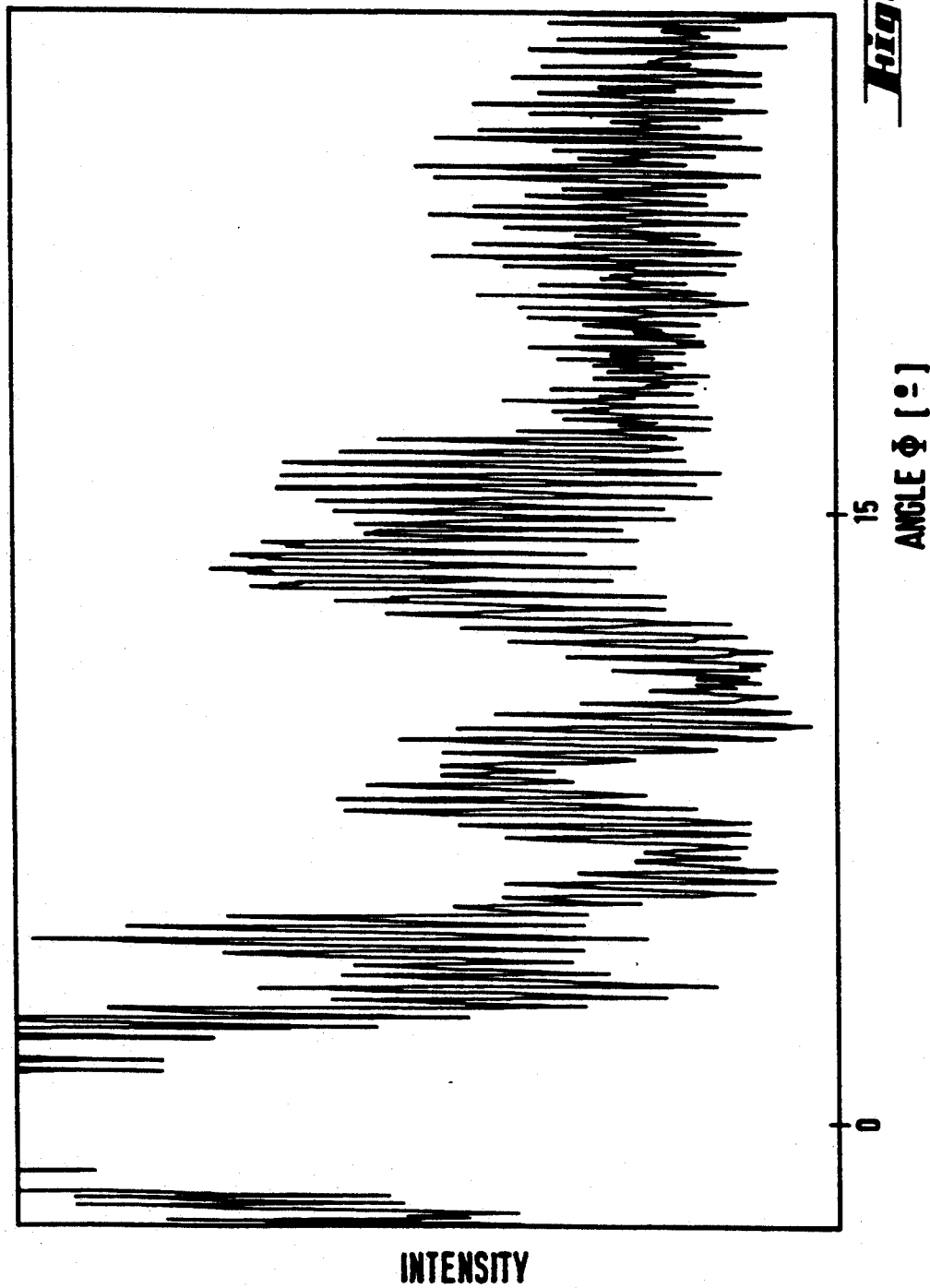

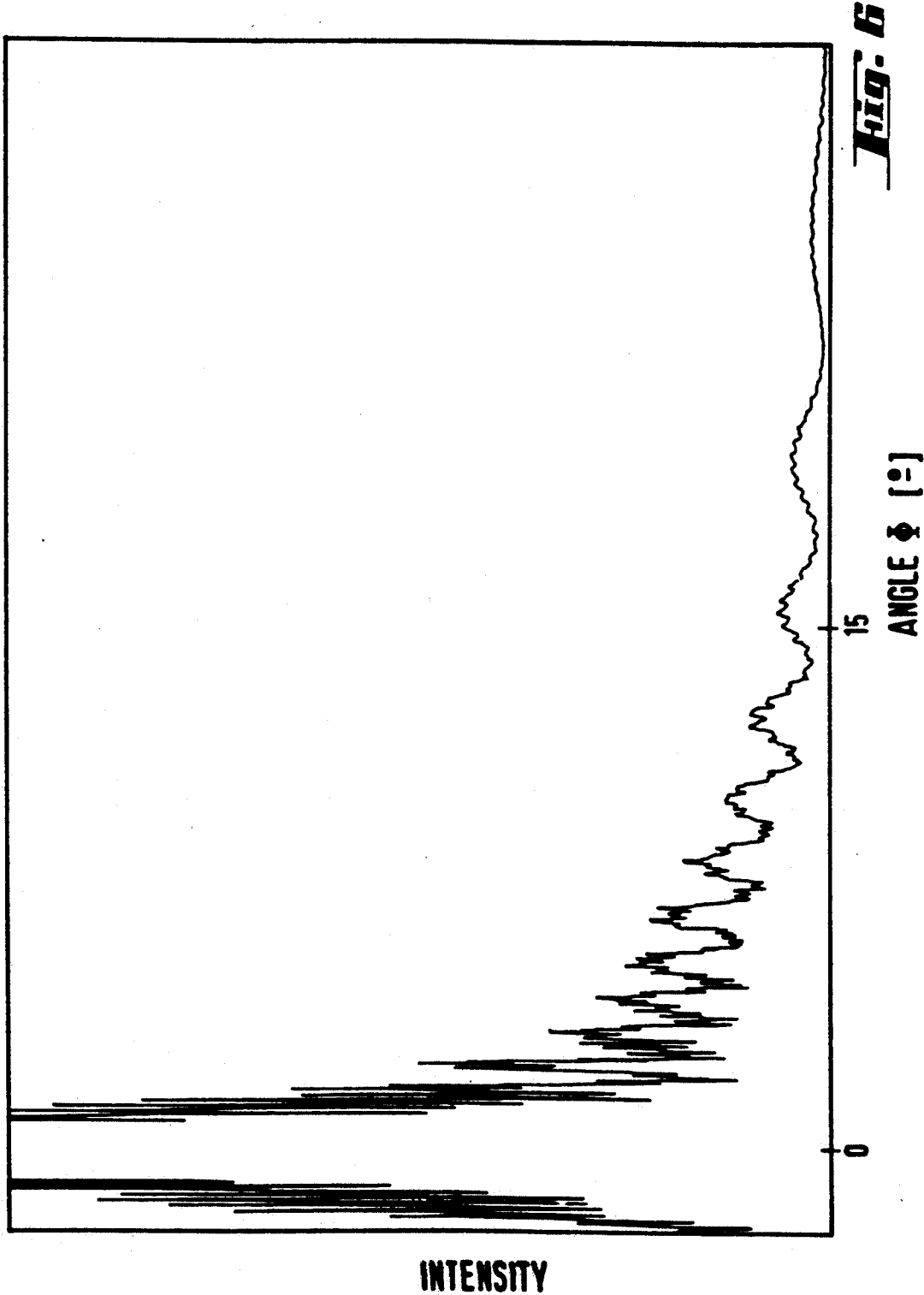

INTERFEROMETRIC MEASURING ARRANGEMENT FOR REFRACTIVE INDEX MEASUREMENTS IN CAPILLARY TUBES

This application is a continuation of application Ser. No. 07/641,192, filed Jan. 15, 1991 now abandoned.

BACKGROUND OF THE INVENTION

The invention relates to an interferometric measuring arrangement, preferably for use in chromatography, especially a device for detecting changes in refractive indices in transparent, preferably round, capillaries, by means of interferometric methods according to the precharacterising clause of patent claim 1.

Refractive index detectors are employed in liquid chromatography and especially for HPLC, SFC, FIA and CE uses. The detectors employed can generally be used universally, except where the substance to be investigated has exactly the same refractive index as the liquid in which the substance is present in dissolved form. The solution is generally referred to as the medium or the so-called mobile phase. The refractive index detector which underlies the invention and is used for measuring changes in refractive index is based on interferometry, especially for chromatographic techniques using capillaries. The capillary is used as the optical element in the production of the necessary interferogram. The important problems that arise when such detectors are used concern their low degree of sensitivity and their extreme temperature dependence.

When two beams of the same coherent light source pass along different optical paths and then coincide, amplifying and extinguishing interferences result. The optical path length is defined as the physical path length multiplied by the refractive index. The displacement of the interference pattern can accordingly be used to measure changes in the refractive index in the medium when the physical path length is kept constant. In the present case, the interferences are produced by lateral illumination of the capillary with the coherent light of, for example, a helium-neon laser. An individual laser beam that is directed onto a capillary is usually dispersed in a plane perpendicular to the axis of the capillary. The angle of dispersion of the light intensity profile measured relative to the longitudinal axis of the principal ray is characteristic of the dimensions of the capillary and the refractive index of its walls and the medium located therein.

After impinging on the capillary, the light rays follow different paths, depending on the angle at which they impinge on the wall of the capillary and also depending on the refractive index of the medium. Interference patterns then appear between the deflected rays of different pairings of beams which emerge from the capillary in parallel form. The result is complicated superimposition of interference fringe patterns.

An important problem consists in finding and selecting the interference fringes to be evaluated, because not all interference fringes change when the refractive index of the medium in the capillary changes, such as, for example, interference fringes of rays that bypass the inside of the capillary. Owing to the superimposition of the different interference fringe patterns, it is also very difficult to find a suitable interference fringe (for example one belonging exclusively to one interference group) in order to obtain an undistorted, clear output signal.

SUMMARY OF THE INVENTION

The problem of the present invention is accordingly to provide a device of the type mentioned at the beginning by means of which it is possible to obtain an interference fringe pattern that can be evaluated in a considerably simpler manner. In addition, the temperature stability of the refractive index detector is to be increased.

The problem is solved by an apparatus according to the characterising portion of patent claim 1. In particular, it is proposed that the capillary be surrounded by a transparent material that has a refractive index that, within a tolerance limit of approximately ±25%, corresponds to the refractive index of the capillary wall. That material is preferably a so-called matching fluid. The transparent material may, of course, also be a solid layer of material. Reflections at the outer wall of the capillary are thereby avoided. This means in practice that the resulting interference fringe pattern now depends only on the refractive index of the medium in the capillary tube and, as a result, the interference fringe pattern is simplified (less superimposition) and also the prerequisite for as simple a selection as possible of the suitable interference fringe is provided. The capillary can, for example, be immersed in a simple manner in this transparent matching fluid and it is possible to effect a simple adjustment of the refractive index of the matching fluid, for example by titration. It is also advantageous that, owing to the matching fluid, the customary round capillaries can be used. Although it would also be possible to use capillaries having a plane outer wall and a curved inner surface, that would require special capillaries that are difficult to manufacture at the present time, and, where they can be manufactured, the extra cost involved is unjustifiable.

Especially in cases where a matching fluid that surrounds the capillary is used, it is also possible to control the temperature of the capillary and the medium in a simple and accurate manner. The temperature-control apparatus is advantageously in the form of a heat exchanger which is immersed in the matching fluid; the heat exchanger is preferably a Peltier element. The matching fluid at the same time acts as a temperature-control bath for the capillary so that the stability of the temperature is substantially increased.

Additional developments of the invention are indicated in the other dependent claims. The invention, with its essential details, is explained in detail hereinafter with reference to the drawings.

BRIEF DESCRIPTION OF THE DRAWINGS

FIGS. 5 and 6 show examples of interferograms.

DETAILED DESCRIPTION OF THE INVENTION

Figure 1:
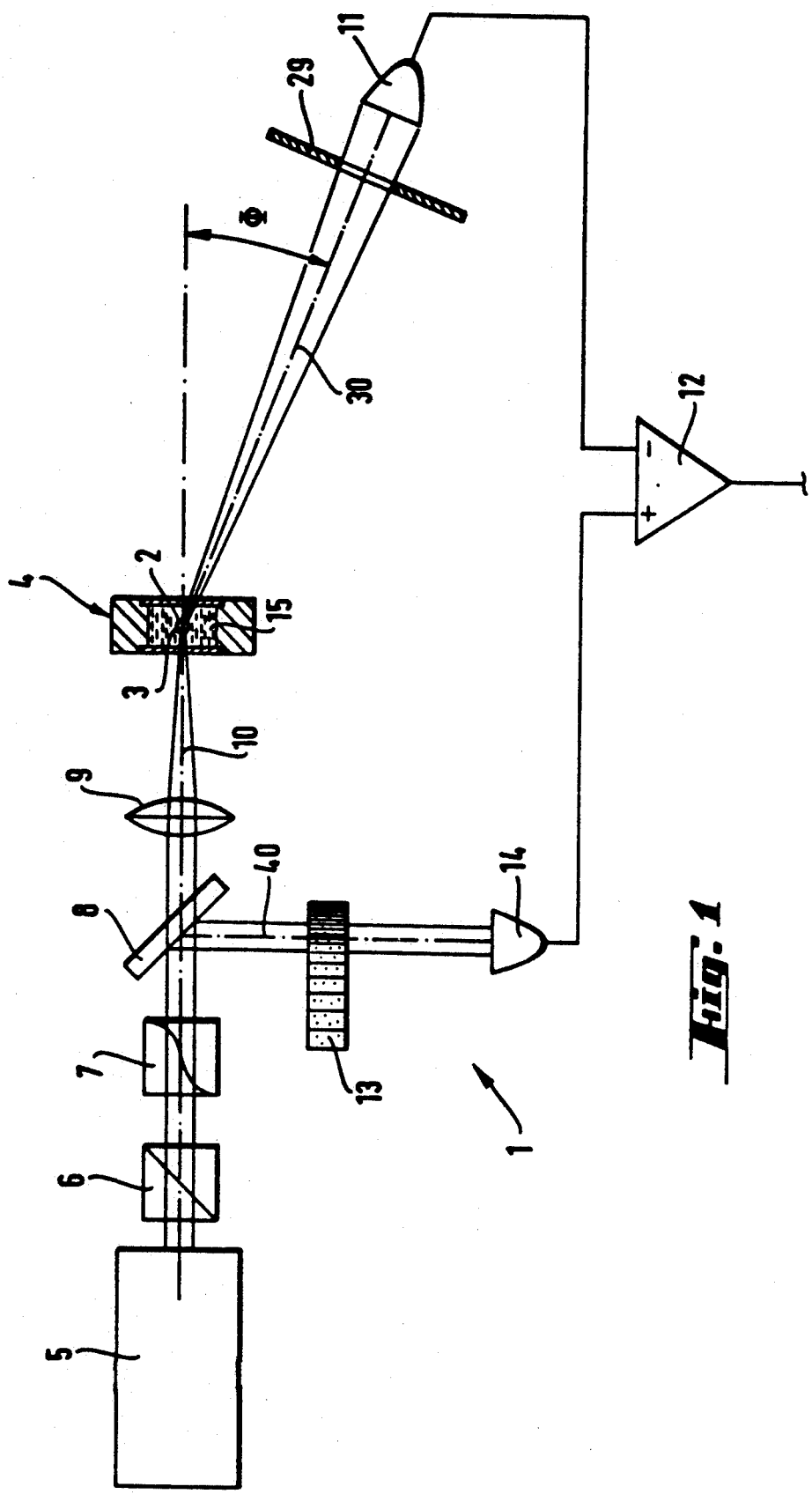
FIG. 1 is a diagrammatic view of a measuring device.

The change in the refractive index of a medium 3 located in a capillary can be determined using the measuring arrangement 1 shown in FIG. 1. The capillary 2 is arranged inside a refractive index detection cell 4. A helium-neon laser 5 is used as the coherent light source.

A polariser 6, a λ/4 plate 7 as well as a beam splitter 8 and a microscope objective 9 are arranged in succession in the path of rays. The main portion 10 of the coherent light passes through the beam splitter 8 and on via the microscope objective 9 to the detection cell 4. A specific interference fringe pattern is obtained depending on what medium is contained in the capillary 2.

An interference fringe 30 is selected from the interference fringe pattern by means of a detector, preferably a photodiode 11, which is preferably pivotable about the capillary 2 as the axis. A slit 29 defines the spatial extent of the interference fringe 30 so that only a portion of the light of the selected interference fringe 30 impinges on the photodiode 11. The second portion 40 of the coherent light, which is split off in the beam splitter 8, serves wedge filter 13 and conveyed to a reference photodiode 14. The signal produced by the interference fringe 30 in the photodiode 11 and the signal produced by the reference beam 40 in the reference photodiode 14 are fed to a differential amplifier 12 and compared with one another. Thus far the measuring arrangement corresponds to commercially available devices, for example the one described in an article by D. J. Bornhop & N. J. Dovichi in Anal. Chem., 1986, 58, page 504.

In order to record a greater area of the interference fringe pattern being produced, the slit 29 and the photodiode 11 are pivoted about the axis of the capillary, and the output signal of the differential amplifier 12 is recorded as a function of the pivoting angle $\phi$ (FIGS. 5 and 6).

In order to simplify the developing interference fringe pattern, the capillary 2 is surrounded according to the invention by a transparent material that has the same refractive index as the wall of the capillary 2. According to the embodiment shown in FIGS. 1 to 4, the capillary 2 is arranged in a matching fluid 15 the refractive index of which corresponds to that of the material of the capillary (normally fused silica) within a tolerance limit of approximately ±25%. Reflections and refractions at the outside of the capillary 2 are thereby largely avoided. Accordingly, the superimpositions that occur are also reduced so that an interference pattern is available that is considerably simplified for the purpose of evaluation. The refractive indices of the capillary material and the matching fluid are preferably approximately the same and then reflections and refractions at the outside of the capillary are entirely avoided and superimpositions are completely prevented.

FIGS. 5 and 6 show recorded interference patterns as a function of the pivoting angle $\phi$ of the photodiode 11. FIG. 5 shows an example of a measurement carried out without the matching fluid 15 while FIG. 6 shows the results of measurements carried out with the matching fluid 15. It can be clearly seen that surrounding the capillary with a layer of matching material, preferably the matching fluid 15, results in a considerable simplification of the interference fringe pattern or the recorded output signals of the photodiode 11.

Figure 4:
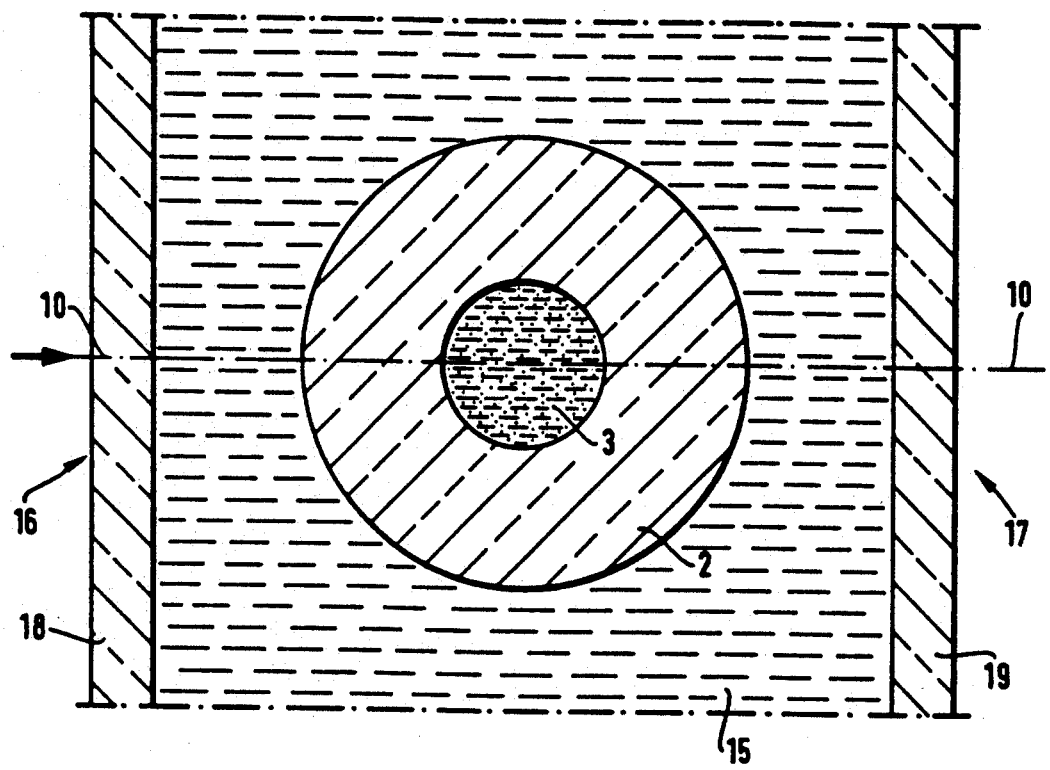
FIG. 4 is a diagrammatic cross-section through a capillary and the matching fluid surrounding it.

FIG. 4 shows diagrammatically a cross-section through the capillary 2 and the matching fluid 15 surrounding it. The light-inlet side 16 and the light-outlet side 17 are preferably plane-parallel faces. The light beam is indicated by its principal ray axis 10. As already mentioned, the refractive index of the matching fluid 15 is matched to that of the material of the capillary within a tolerance limit of ±25%. The refractive index of the matching fluid used can be matched, for example, by titration. For that purpose, a transparent, organic solution having a refractive index that is slightly lower than that of the material of the capillary can continue to be changed by titration with another solution that has a refractive index slightly higher than that of the material of the capillary until, on immersing a portion of the capillary in the titrated solution, the capillary can no longer be seen.

Figure 2:
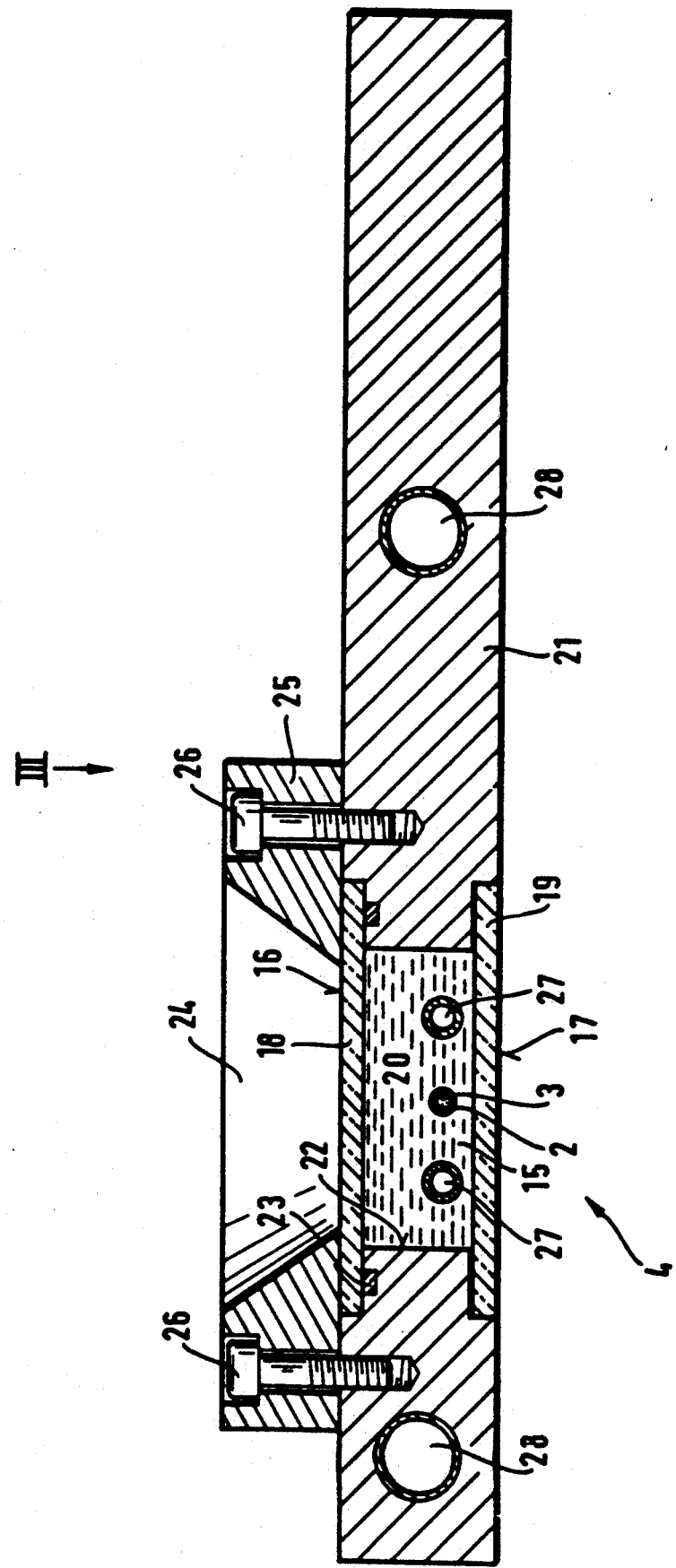
FIG. 2 is a sectional view along line II—II in FIG. 3 of a detection cell with the reference numeral 4.
Figure 3:
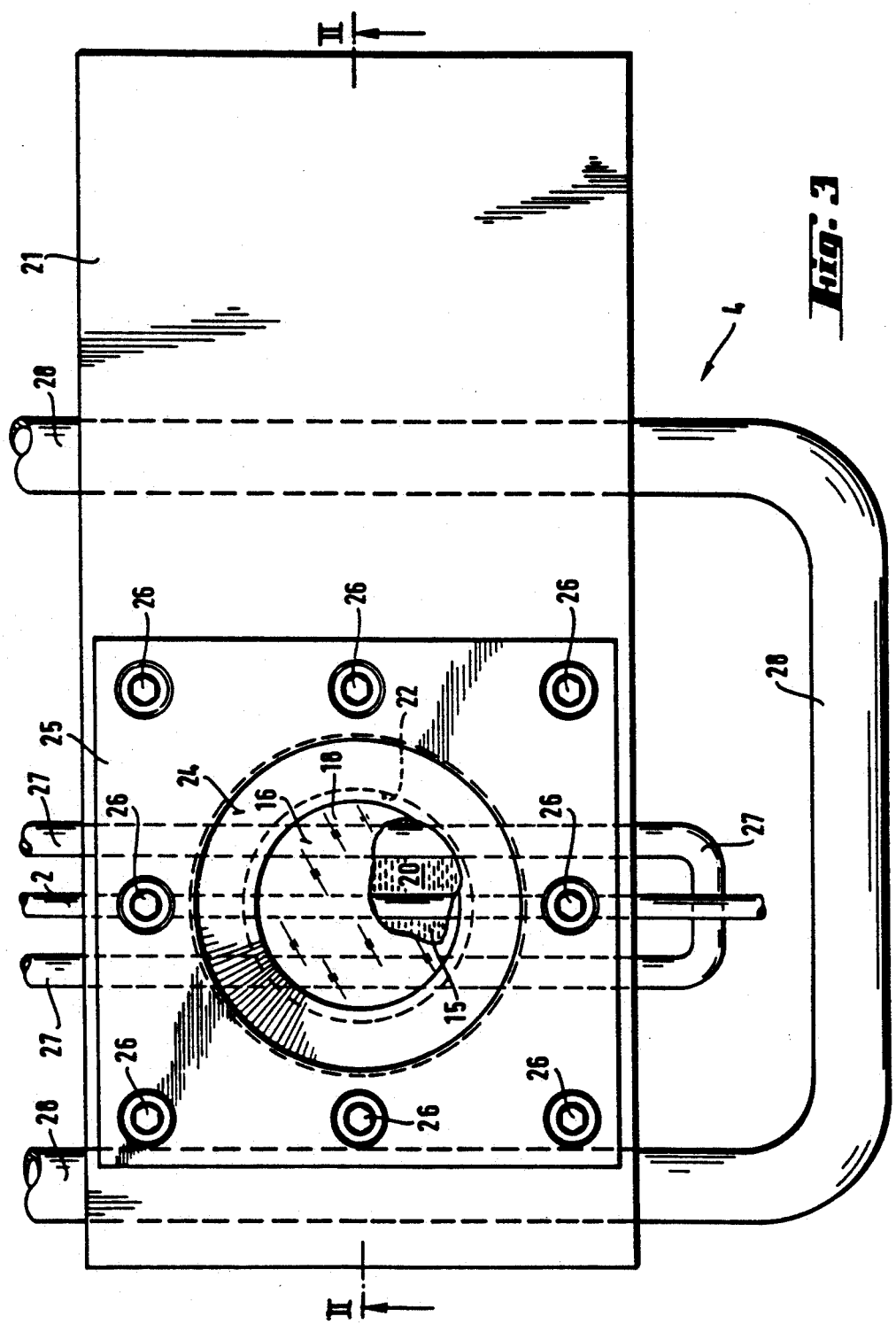
FIG. 3 is a view of the detection cell from the direction of the arrow III in FIG. 2.

FIGS. 2 and 3 show the structure of a detection cell 4. The matching fluid 15 and the capillary 2 are arranged in a chamber 20 delimited by plane-parallel glass plates 18, 19 arranged opposite one another. A metal block 21 consisting preferably of aluminium is used as a housing. This plate-shaped metal block has a through-opening 22 in order to form the chamber 20. One side of this through-opening 22 is formed by the glass plate 19 which is connected fixedly and sealingly to the housing. The glass plate is preferably glued in. The opposite side of the through-opening 22 is formed by the other, releasably arranged glass plate 18, one flat side of which rests on a sealing ring 23 formed by an O-ring. Pressure is applied to the other flat side of this glass plate 18 by a holding plate 25 which leaves open a passage window 24. The holding plate is connected to the metal block 21 by means of screws 26.

In order to increase the temperature stability, the temperature of the capillary is controlled. In a particularly advantageous manner, the matching fluid 15 is for that purpose used simultaneously as a temperature-control bath. A heat exchanger 27, which is immersed in the matching fluid 15, is used to regulate the temperature. The temperature of the metal block 21 is also controlled, for which purpose a fluid-carrying tube 28 is provided according to the embodiment shown. It is also advantageous that, owing to the comparatively large mass of the metal block and owing to the use of a material having good heat-conducting properties, heat fluctuations are buffered. The heat exchanger 27 and the tube 28 are connected to external temperature-control baths. In an especially preferred method of temperature control, for example electrical temperature regulation by means of one or more Peltier elements can also be provided. Owing to the temperature-control measures provided, a temperature stability as good as $2.5 \times 10^{-2}$K can be achieved. The control of the temperature of the capillary 2 by means of the matching fluid 15 offers, in particular, the great advantage that it takes place directly in the optically relevant portion of the measuring apparatus and is not, as in the case of the apparatuses known hitherto, arranged upstream or downstream of the actual measuring region.

The interferometric measuring arrangement according to the invention described with reference to the special case of the measurement of changes in refractive index can, however, also be used for measurements in the ultraviolet range or in the infrared range. It is also well suited to fluorescence uses, especially for measurements of laser-induced fluorescence. The choice of the layer of matching material depends also on the type of radiation used and the transparency of the material to this radiation.

The radiation normally used lies in the wavelength range of from approximately 150 nm to approximately 5000 nm. This fact alone that it can be used in a very wide range of the electromagnetic spectrum demonstrates the universal applicability of the interferometric measuring arrangement according to the invention.

In all, the use of a layer of matching material, the refractive index of which is within a tolerance limit of ±25% of the refractive index of the material of the capillary, renders possible, in a simple manner, a considerable reduction and even prevention of interfering reflections and refractions of the measuring light at the outside of the capillary. By selecting a layer of material having a thermal-conduction coefficient that is at least slightly greater than that of the surrounding medium (normally air), the temperature stability of the measuring arrangement can also be significantly increased.

What is claimed is:

1. A refractive index monitoring apparatus having a radiation-permeable, preferably round capillary tube with a radiation inlet side and a radiation outlet side, for accommodating a sample flowing therethrough, and having an interferometric device which comprises a source of radiation and a photoelectric detector sensitive to said radiation;

said capillary tube being arranged in the path of said radiation between said source of radiation and said photoelectric detector, and, at least on said radiation-inlet side, said capillary tube being surrounded by a layer of material that is permeable to said radiation and that has a refractive index that, within a tolerance limit of approximately ±25%, corresponds to that of the wall-material of said capillary tube;

said interferometric device being adapted to produce an interference pattern upon said radiation passing through said sample flowing through said capillary tube, said interference pattern being generated in the path of said radiation on the side of said detector;

and said photoelectric detector being adapted to monitor changes of said refractive index pattern responsive to changes of the refractive index of said sample flowing through said capillary tube.

2. An apparatus according to claim 1, wherein said layer of material is a matching fluid which surrounds said capillary on said radiation-inlet side and on said radiation-outlet side.

3. An apparatus according to claim 2, wherein said layer of material has light-inlet and light-outlet faces which are both plane and are arranged preferably parallel to one another.

4. An apparatus according to claim 1, wherein said matching fluid and said capillary are arranged in a chamber delimited by (plane-)parallel glass plates arranged opposite one another.

5. An apparatus according to claim 4, wherein a temperature-control apparatus is provided for, especially thermostatic, temperature-control of said capillary.

6. An apparatus according to claim 5, wherein said temperature-control apparatus has a tube that carries a temperature-control medium and passes through said matching fluid, or has some such heat-exchanger.

7. An apparatus according to claim 5, wherein said temperature-control apparatus has electrical temperature regulation, preferably by means of a Peltier element.

8. An apparatus according to claim 4, wherein said chamber is arranged in a preferably temperature-controlled metal block consisting preferably of aluminium.

9. An apparatus according to claim 8, wherein said metal block has one or more tubes that are connected to an external temperature-control bath or are constructed to accommodate a temperature-controlled fluid.

10. An apparatus according to claim 9, wherein two glass plates are delimiting said chamber one of said glass plates being connected fixedly and said other glass plate being connected releasably to said metal block or the like housing.

11. An apparatus according to claim 10, wherein said fixed glass plate is sealingly cemented or connected in suchlike manner to said housing, and said other, releasable glass plate rests with one flat side on a sealing ring, especially an O-ring, and pressure is applied to it via its other flat side by a holding plate that can be connected, especially screwed, to said housing and that leaves open a passage window.

12. An apparatus according to claim 1, wherein said radiation used has a wavelength of from approximately 150 nm to approximately 5000 nm.

13. An apparatus according to claim 1, wherein said radiation used is coherent.

14. An apparatus according to claim 1, wherein said refractive index of said layer of material corresponds to that of said material of said capillary.

15. An apparatus according to claim 1, wherein said layer of material has a thermal-conduction coefficient that is greater than that of air.

* * * * *